United States Patent [19]

Ishikawa et al.

[11] 4,141,249
[45] Feb. 27, 1979

[54] SUB-LANCE ASSEMBLY FOR SAMPLING AND TEMPERATURE-MEASURING OF MOLTEN METAL DURING REFINING

[75] Inventors: Kenkichi Ishikawa; Shinobu Kumagai; Teruyuki Hasegawa; Akiyoshi Sakamoto, all of Fukuyama, Japan

[73] Assignee: Nippon Kokan Kabushiki Kaisha, Tokyo, Japan

[21] Appl. No.: 882,188

[22] Filed: Feb. 28, 1978

[30] Foreign Application Priority Data

Mar. 14, 1977 [JP] Japan .............................. 52-26942
Mar. 18, 1977 [JP] Japan ........................... 52-31985[U]

[51] Int. Cl.² .............................................. G01N 1/12
[52] U.S. Cl. ................................. 73/423 R; 73/421 B;
73/425.4 R; 73/432 A; 73/DIG. 9
[58] Field of Search ............. 73/339 R, 421 R, 421 B,
73/423 R, 425.4 R, 432 A, DIG. 9

[56] References Cited

U.S. PATENT DOCUMENTS

| 3,494,200 | 2/1970 | Mihalon et al. ................ 73/DIG. 9 |
| 3,572,124 | 3/1971 | Nagaoka et al. ............... 73/DIG. 9 |
| 3,717,034 | 2/1973 | Dukelow et al. ............... 73/DIG. 9 |
| 3,824,837 | 7/1974 | Nagaoka et al. ............... 73/DIG. 9 |

FOREIGN PATENT DOCUMENTS

129604 10/1977 Japan .................................. 73/DIG. 9

*Primary Examiner*—Charles Gorenstein
*Attorney, Agent, or Firm*—Flynn & Frishauf

[57] ABSTRACT

A sub-lance assembly for sampling and temperature-measuring of molten metal during refining in a top-blowing oxygen converter, which comprises: a sub-lance having a concentric three-pipe structure comprising from inside to outside an air supply pipe, a water discharge pipe and a water supply pipe; a water supply outer cylinder having a water supply branch pipe, rotatably engaging with the upper end portion of said water supply pipe; a water discharge outer cylinder having a water discharge branch pipe, rotatably engaging with the upper end portion of said water discharge pipe; said water supply branch pipe and said water discharge branch pipe being integrally connected together by a fixing plate; a drive mechanism fitted onto the outer surface of said water supply outer cylinder or said water discharge outer cylinder, for rotating said sub-lance around the axial line thereof; and a sub-lance rotation angle detector at the tip of the axis of rotation of said drive mechanism, for detecting the angle of rotation of said sub-lance.

4 Claims, 9 Drawing Figures

SUB-LANCE ASSEMBLY FOR SAMPLING AND TEMPERATURE-MEASURING OF MOLTEN METAL DURING REFINING

FIELD OF THE INVENTION

The present invention relates to a sub-lance assembly for sampling and temperature-measuring of molten metal during refining in a top-blowing oxygen converter.

BACKGROUND OF THE INVENTION

In the field of refining of molten metal in a top-blowing oxygen converter, a control system based on the dynamic control has been developed for the purpose of saving labor in refining operations and automating the processes. A sub-lance for obtaining information and data concerning conditions of refining in the converter such as the chemical composition and the temperature of molten metal during refining is indispensable for said control system.

Figures 1, 2, 3:
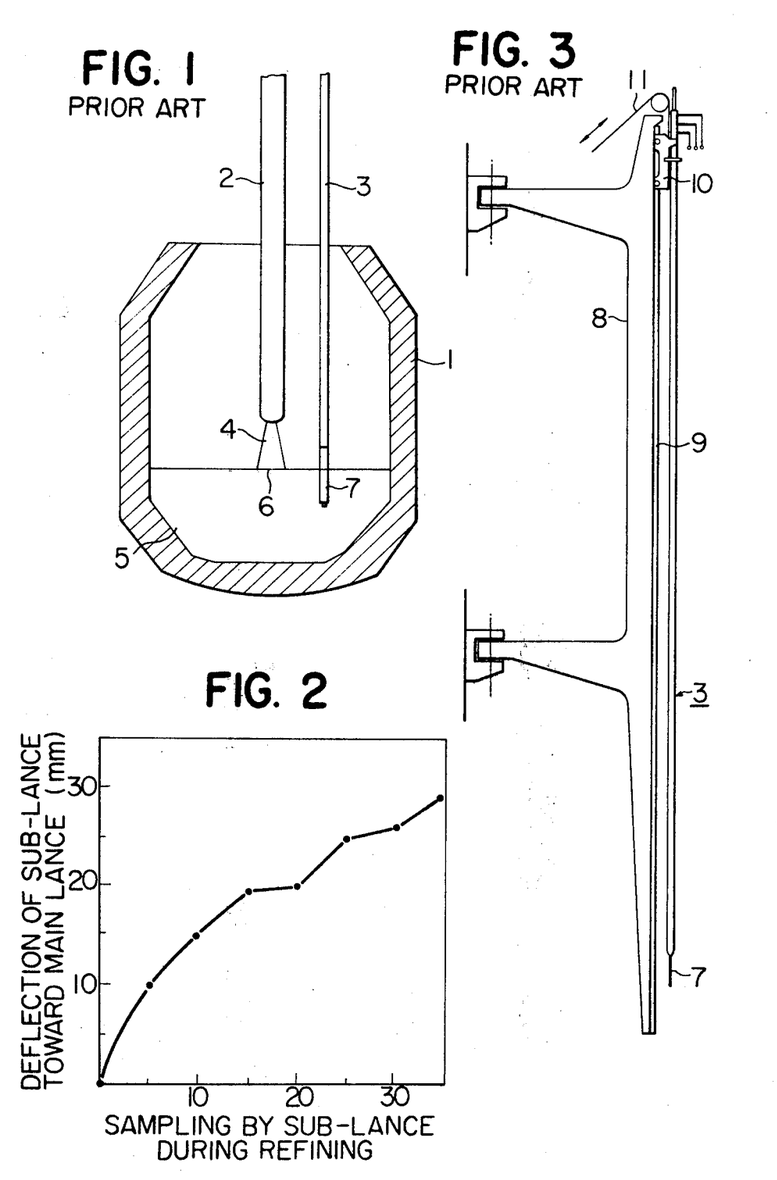
FIG. 1 is a schematic sectional view illustrating an example of application of a sub-lance in a prior art top-blowing oxygen converter.
FIG. 2 is a graph illustrating the relation between the number of repetitions of use of a sub-lance during refining of molten metal in a prior art top-blowing oxygen converter and the deflection of said sub-lance toward the main lance.
FIG. 3 is a schematic drawing illustrating a prior art manner of fitting a sub-lance assembly and manner of vertical movement of same.

FIG. 1 is a schematic sectional view illustrating an embodiment of the aforementioned sub-lance. As shown in FIG. 1, a molten metal 5 is refined by inserting downward a main lance for blowing oxygen 2 substantially vertically into a top-blowing oxygen converter 1 containing a molten metal 5 to be refined, and by blowing pressurized oxygen onto the surface of said molten metal 5 through said main lance 2 at a certain position above the surface of said molten metal 5. On the other hand, sampling and temperature-measuring of said molten metal 5 are carried out by inserting downward a sub-lance 3 into said converter 1 substantially vertically at a proper timing, and by immersing a probe 7 for sampling and temperature-measuring of said molten metal 5, which is releasably fitted to the lowermost end of said sub-lance 3, into said molten metal 5.

In general, the sub-lance 3 is releasably fitted to a sub-lance carriage 10 as shown in FIG. 3. The sub-lance carriage 10 is suspended by a wire rope 11 and moves vertically together with the sub-lance 3 along a guide rail 9 provided on a turning frame 8 by hoisting up or down said wire rope 11 with the use of a winch (not shown). Sampling and temperature-measuring of said molten metal 5 in the converter 1 are therefore conducted by lowering the sub-lance 3 together with the sub-lance carriage 10 by hoisting down the wire rope 11 with the use of the winch, and by immersing the probe 7 fitted to the lowermost end of the sub-lance 3 into the molten metal 5. The sub-lance 3 is movable, as required, together with the sub-lance carriage 10, from outside to above the converter 3 and from above the converter 3 to outside, by turning the turning frame 8.

The sub-lance 3 usually has a concentric three-pipe structure comprising from inside to outside an air supply pipe, a water discharge pipe and a water supply pipe, and is cooled by cooling water during sampling and/or temperature-measuring the molten metal 5. To prevent slag from coming into the probe 7 when the probe 7 passes through the slag layer covering the surface of the molten metal 5, pressurized gas such as air and nitrogen is blown into the probe 7 through the air supply pipe.

However, the sub-lance 3 inserted into the converter 1 during refining of the molten metal 5 deflects inevitably toward the main lance 2 under the effect of the high temperature heat of the hot spot 6 where occur reactions between oxygen 4 blown from the main lance 2 and the molten metal 5 and the high temperature heat of molten metal and molten slag splashing and adhering onto the sub-lance 3. More specifically, as shown in the graph of FIG. 2, the sub-lance 3 deflects toward the main lance 2, under the effect of the above-mentioned heat affection, substantially in proportion to the number of repetitions of sampling and/or temperature-measuring during refining of the molten metal. Because of this deflection, it has been unavoidable that the following problems occurred in a conventional sub-lance 3 after being used several times:

(1) It becomes difficult to immerse straight vertically the probe 7 fitted to the lowermost end of the sub-lance 3 into the molten metal 5, and this causes troubles in sampling and/or temperature-measuring;

(2) The sub-lance 3 and the probe 7 become too close to the hot spot 6, or even come in the hot spot 6, thus causing burnout of the sub-lance 3 and the probe 7;

(3) The device (not shown) for engaging and disengaging the probe 7 with the lowermost end of the sub-lance 3 becomes unserviceable; and (4) It becomes impossible for the sub-lance 3 to pass through a through-hole provided in a hood (not shown) which hangs over and covers the converter 1, and when the aforementioned deflection of the sub-lance 3 is serious, it may become necessary to remove the sub-lance 3 by flame cutting.

To avoid these inconveniences, prevention of the above-mentioned deflection of the sub-lance toward the main lance has been attempted through such measures as the enhancement of cooling of the sub-lance and the prevention of molten metal and molten slag from adhering onto the sub-lance. It was however impossible to ensure prevention of the aforementioned deflection of the sub-lance through these measures.

With a view to solving the above-mentioned problems involved in the conventional sub-lance, Japanese Patent Provisional Application No. 129,604/77, laid open on Oct. 31, 1977, discloses a method for sampling and temperature-measuring with a sub-lance, which comprises, after a certain number of repetitions of sampling and/or temperature-measuring, rotating the sub-lance around its axial line by about 180°, i.e., up to the direction just opposite to the direction of deflection of the sub-lance, and conducting sampling and/or temperature-measuring in the latter position several times, thus correcting the deflection toward the main lance (said method is hereinafter referred to as the "prior art").

Figures 4, 9:
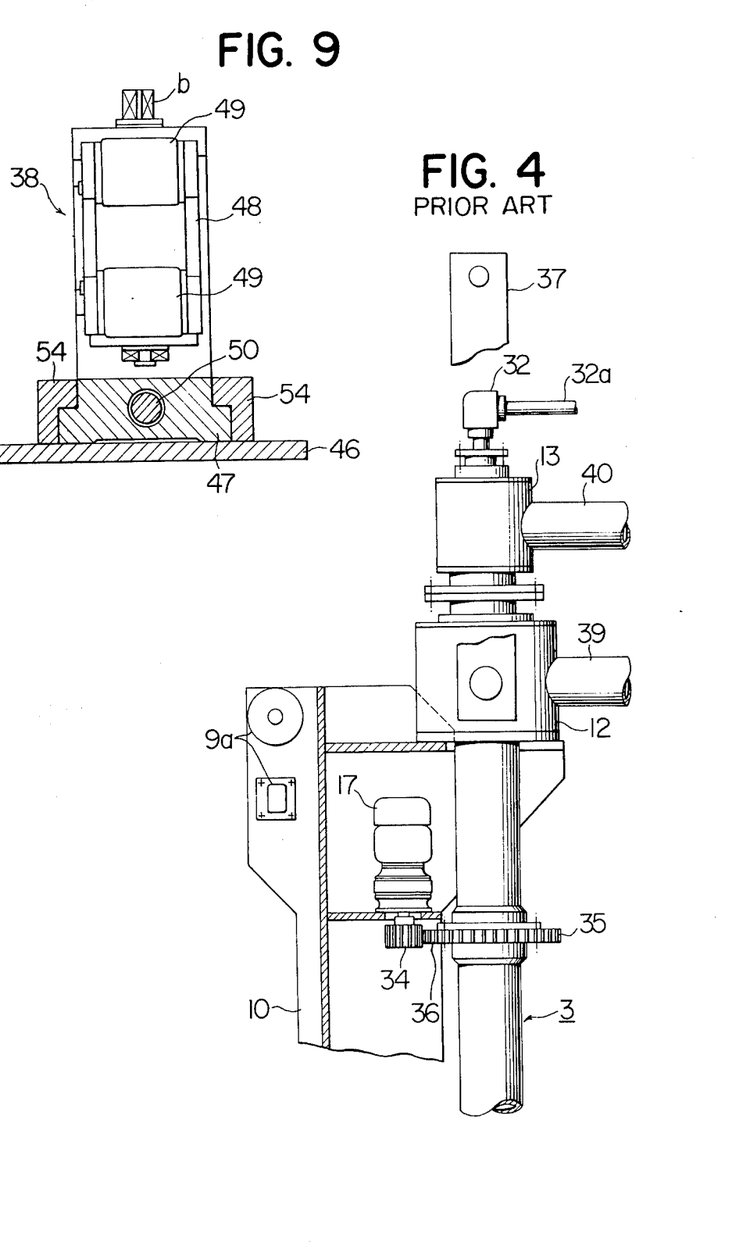

According to said prior art, as shown in FIGS. 3 and 4, a sub-lance 3 is fitted to a sub-lance carriage 10, rotatably around the axial line of said sub-lance 3 and releasably from the sub-lance carriage 10. The sub-lance carriage 10, which is suspended by a wire rope, is vertically movable together with the sub-lance 3 along a guide rail 9 provided on a turning frame 8, through guide rollers 9a, by hoisting up or down the wire rope 11 through a winch (not shown).

The sub-lance 3 has a concentric three-pipe structure comprising from inside to outside an air supply pipe, a water discharge pipe and a water supply pipe. A water supply outer cylinder 12 having a water supply branch pipe 39 rotatably engages with the upper end portion of said water supply pipe through a bearing mechanism and a sealing mechanism. A water discharge outer cylinder 13 having a water discharge branch pipe 40 rotatably engages with the upper end portion of said water discharge pipe through a bearing mechanism and a sealing mechanism. When conducting sampling and/or temperature-measuring, the sub-lance 3 is cooled by cooling water which is supplied through the water supply branch pipe 39, the water supply outer cylinder 12 and the water supply pipe, and is discharged through the water discharge pipe, the water discharge outer cylinder 13 and the water discharge branch pipe 40. A probe 7 for sampling and temperature-measuring of molten metal is connected to the lowermost end of the air supply pipe, and a swivel joint 32 having an air supply branch pipe 32a rotatably engages with the upper end portion thereof. The air supply pipe, the water discharge pipe and the water supply pipe constituting the sub-lance 3 are fixed to each other by an appropriate means through a sealing mechanism. Therefore, when rotating the sub-lance 3 around the axial line thereof in a manner as described later, the air supply pipe, the water discharge pipe and the water supply pipe rotate as an integral body, and the water supply outer cylinder 12, the water discharge outer cylinder 13 and the swivel joint 32 never rotate together with the sub-lance 3. Even while rotating the sub-lance 3, therefore, it is possible to supply and discharge water and to supply air always at a prescribed position.

In FIG. 4, 17 is a drive mechanism including a reduction gear for rotating the sub-lance 3 around the axial line thereof. A chain 36 engages with a small sprocket 34 fitted to the axis of rotation of the drive mechanism 17 and with a large sprocket 35 fitted to the sub-lance 3, and permits rotation of the sub-lance 3 around the axial line thereof up to a desired angle by driving the drive mechanism 17. It is therefore possible to correct a deflection of the sub-lance 3, after using the sub-lance 3 several times for sampling and/or temperature-measuring during refining a molten metal in the converter, by ascertaining the direction and the degree of deflection of the sub-lance 3, then rotating the sub-lance 3 up to a direction opposite to the direction of deflection, i.e., by about 180°, and conducting sampling and/or temperature-measuring several times at the latter position. It is known that the drive mechanism 17, which is fitted to the sub-lance carriage 10 in FIG. 4, may be fitted to the water supply outer cylinder 12 or the water discharge outer cylinder 13. It is also known that the drive mechanism 17 may be actuated by remote operation.

In FIG. 4, 37 is a suspension fitting fixed to the upper end portion of the water discharge outer cylinder 13. The sub-lance 3 can be engaged with or disengaged from the sub-lance carriage 10 by hoisting up or down the suspension fitting 37 by a crane (not shown). More specifically, it is possible to easily engage the sub-lance 3 with the sub-lance carriage 10 by hoisting down the sub-lance 3 with the use of the crane and inserting the sub-lance 3 through a hole provided in a receiving stand (not shown) fixed to the upper end portion of the sub-lance carriage 10 and through a hole provided in a supporting device (not shown) fixed to the lower end portion of the sub-lance carriage 10. Sub-lance 3 can easily be disengaged from the sub-lance carriage 10 by hoisting up, with the use of the crane, the sub-lance 3 engaged with the sub-lance carriage 10 as mentioned above.

According to the prior art described above, it is possible to correct a deflection of the sub-lance toward the main lance occurring during refining of molten metal in a coverter. While it had been necessary to replace about 12 sub-lances per 1,000 times of sampling and/or temperature-measuring, said prior art eliminated the necessity of replacing the sub-lance after the same number of repetitions of sampling and/or temperature-measuring, and permitted sampling and/or temperature-measuring in a satisfactory condition, thus giving remarkable effects.

However, said prior art has the following drawbacks:

(1) As mentioned above, the water supply outer cylinder 12 and the water discharge outer cylinder 13 respectively engage rotatably with the water supply pipe and the water discharge pipe through a bearing mechanism and a sealing mechanism. Furthermore, the air supply pipe, the water discharge pipe and the water supply pipe constituting the sub-lance 3 are fixed to each other by an appropriate means through a sealing mechanism. However, when rotating the sub-lance 3 by the drive mechanism 17, a strong non-uniform force is applied to these sealing mechanisms, causing troubles in these sealing mechanisms, and thus may cause leakage of cooling water, a serious accident;

(2) When rotating the sub-lance 3 around the axial line thereof by the drive mechanism 17, it is not always easy to accurately detect the angle of rotation of the sub-lance 3. For this reason, it is difficult to rotate the sub-lance 3 by an appropriate angle of rotation for correcting the above-mentioned deflection of the sub-lance 3;

(3) Along with the recent trend of top-blowing oxygen converters becoming larger in size, the length of the sub-lance 3 also tends to increase even to over 20 meters in some cases. Even such a long sub-lance is fitted at the upper end portion thereof to a sub-lance carriage only at two points. It is therefore difficult not only to prevent swinging of the sub-lance during operation but also to align the sub-lance for holding it accurately in the vertical position.

Because of these drawbacks, said prior art was problematic, in spite of the excellent advantages as mentioned above, in that these advantages could not be fully utilized.

SUMMARY OF THE INVENTION

An object of the present invention is therefore to provide an improved sub-lance assembly for sampling and temperature-measuring of a molten metal during refining of the molten metal in a top-blowing oxygen converter, which can be used many times.

Another object of the present invention is to provide an improved sub-lance assembly including a sub-lance rotatable around the axial line thereof.

A principal object of the present invention is to provide an improved sub-lance assembly including a sub-lance rotatable around the axial line thereof, said improved sub-lance assembly permitting sure correction of the deflection of the sub-lance by accurately detecting the angle of rotation of the sub-lance, complete prevention of leakage of cooling water for cooling the sub-lance, easy and sure alignment for holding the sub-lance in the vertical position, and prevention of swinging of the sub-lance.

In accordance with the present invention, in a sub-lance assembly for sampling and temperature-measuring of a molten metal during refining, which comprises:

a sub-lance having a concentric three-pipe structure comprising from inside to outside an air supply pipe, a water discharge pipe and a water supply pipe, said sub-lance being releasably fitted to a sub-lance carriage in the substantially vertical position by a receiving stand fixed to the upper end portion of said sub-lance carriage and a supporting device fixed to the lower end portion of said sub-lance carriage;

a water supply outer cylinder having a water supply branch pipe, rotatably engaging with the upper end portion of said water supply pipe through a bearing mechanism and a sealing mechanism, said water supply pipe, said water supply outer cylinder and said water supply branch pipe communicating with each other in a water-tight manner;

a water discharge outer cylinder having a water discharge branch pipe, rotatably engaging with the upper end portion of said water discharge pipe through a bearing mechanism and a sealing mechanism, said water discharge pipe, said water discharge outer cylinder and said water discharge branch pipe communicating with each other in a water-tight manner, said water discharge outer cylinder being located above said water supply outer cylinder; and, a drive mechanism for rotating said sub-lance around the axial line thereof, said drive mechanism being fitted onto one of the outer surfaces of said water supply outer cylinder and said water discharge outer cylinder;

there is provided the improvement characterized by:

providing a sub-lance rotation angle detector at the tip of the axis of rotation of said drive mechanism, said rotation angle detector being adapted to detect the angle of rotation of said sub-lance; and, integrally connecting said water supply branch pipe and said water discharge branch pipe by a fixing plate at a place near said water supply outer cylinder and said water discharge outer cylinder, said fixing plate being adapted, when rotating said sub-lance by said drive mechanism, to prevent said water supply outer cylinder and said water discharge outer cylinder from rotating together with said sub-lance.

BRIEF DESCRIPTION OF THE DRAWINGS

FIG. 4 is a partial cutaway front view of the sub-lance assembly of the prior art;

DETAILED DESCRIPTION OF PREFERRED EMBODIMENTS

We conducted intensive studies to solve the problems involved in said prior art. As a result we have found that, in the sub-lance assembly based on said prior art, it is possible to solve all the problems involved in said prior art by: (a) providing the drive mechanism for the sub-lance with a sub-lance rotation angle detector serving also as a control device, (b) integrally connecting the water supply branch pipe of the water supply outer cylinder and the water discharge branch pipe of the water discharge outer cylinder by a fixing plate, and (c) improving the supporting device for rotatably and releasably fitting the sub-lance to the sub-lance carriage.

The sub-lance assembly of the present invention is described in detail below by means of an example with reference to the drawings.

EXAMPLE

Figure 5:
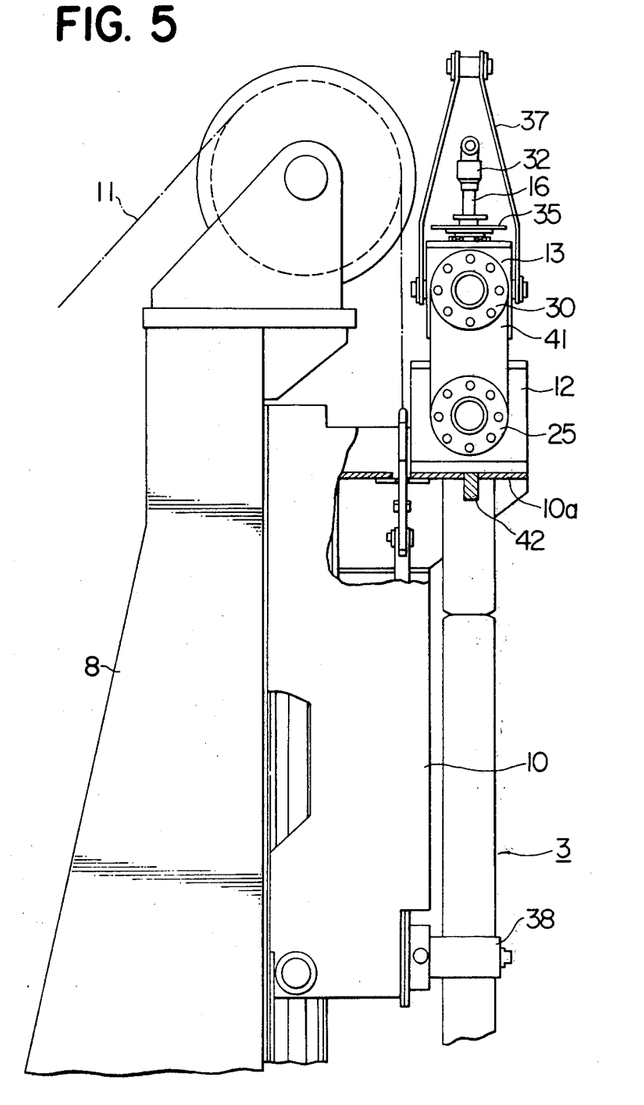
FIG. 5 is a partial cutaway side view illustrating an embodiment of the sub-lance assembly of the present invention.
Figure 6:
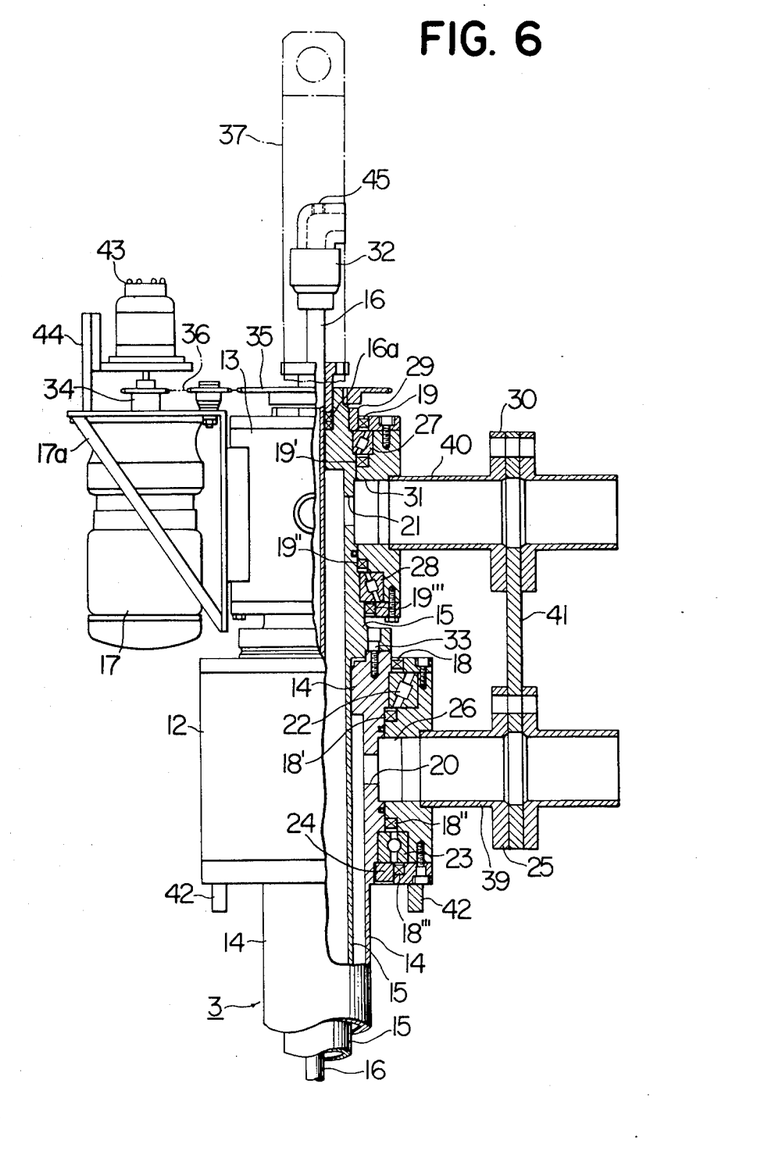
FIG. 6 is a partial cutaway front view illustrating an embodiment of the sub-lance assembly of the present invention.

FIG. 5 is a partial cutaway side view illustrating an embodiment of the sub-lance assembly of the present invention, and FIG. 6 is a partial cutaway front view of same.

In FIGS. 5 and 6, 3 is a sub-lance, 8 is a turning frame, and 10 is a sub-lance carriage. The sub-lance 3 is rotatably and releasably fitted to the sub-lance carriage 10, as described later, by a receiving stand 10a and a supporting device 38 both fixed to the sub-lance carriage 10. The sub-lance carriage 10 is suspended by a wire rope 11, and as mentioned previously with reference to FIG. 3, is vertically movable together with the sub-lance 3 along a guide rail provided on a turning frame 8 by hoisting up or down said wire rope 11 with the use of a winch (not shown). As described previously with reference to FIGS. 1 and 2, a probe for sampling and temperature-measuring of a molten metal is releasably fitted to the lowermost end of the sub-lance 3. Sampling and temperature-measuring of the molten metal are therefore carried out by lowering the sub-lance 3 together with the sub-lance carriage 10 by hoisting down the wire rope 11 with the use of the winch at the time of sampling and temperature-measuring of the molten metal in the converter, and by immersing the probe fitted to the lowermost end of the sub-lance 3 into the molten metal. As has conventionally been known, the sub-lance 3 can be moved, as required, together with the sub-lance carriage 10, from outside to above the converter and from above the converter to outside, by turning the turning frame 8.

As shown in FIGS. 5 and 6, the sub-lance 3 has a concentric three-pipe structure comprising from inside to outside an air supply pipe 16, a water discharge pipe 15 and a water supply pipe 14.

A water supply outer cylinder 12 rotatably engages with the upper end portion of the water supply pipe 14 through bearings 22 and 23. The water supply outer cylinder 12, the water supply pipe 14 and the bearings 22 and 23 are assembled so as not to come off from each other by tightening a tightening nut 24. The gap between the water supply outer cylinder 12 and the water supply pipe 14 is water-tightly sealed by oil seals 18, 18', 18'' and 18'''. A plurality of water supply holes 20 are pierced on the water supply pipe 14 in the circumferential direction, and communicate with an annular groove 26 provided between the outer surface of the water supply pipe 14 and the inner surface of the water supply outer cylinder 12. The water supply outer cylinder 12 is further fitted with a water supply branch pipe 39 having a flange joint 25 for coupling an external cooling water supply pipe (not shown), and the water supply branch pipe 39 communicates with the annular groove 26. Since the water supply pipe 14, the water supply holes 20, the annular groove 26, the water supply outer cylinder 12 and the water supply branch pipe 39 thus communicate with each other in a water-tight manner, cooling water can be supplied into the water supply pipe 14 through the water supply branch pipe 39, the water supply outer cylinder 12, the annular groove 26 and the water supply holes 20 from the external cooling water supply pipe (not shown).

As in the water supply pipe 14 mentioned above, a water discharge outer cylinder 13 rotatably engages with the upper end portion of the water discharge pipe 15 through bearings 27 and 28. The water discharge outer cylinder 13, the water discharge pipe 15 and the bearings 27 and 28 are assembled so as not to come off from each other by tightening a tightening nut 29. The gap between the water discharge outer cylinder 13 and the water discharge pipe 15 is water-tightly sealed by oil seals 19, 19', 19" and 19'". A plurality of water discharge holes 21 are pierced on the water discharge pipe 15 in the circumferential direction, and communicate with an annular groove 31 provided between the outer surface of the water discharge pipe 15 and the inner surface of the water discharge outer cylinder 13. The water discharge outer cylinder 13 is further fitted with a water discharge branch pipe 40 having a flange joint 30 for coupling an external cooling water discharge pipe (not shown), and the water discharge branch pipe 40 communicates with the annular groove 31. Since the water discharge pipe 15, the water discharge holes 21, the annular groove 31, the water discharge outer cylinder 13 and the water discharge branch pipe 40 thus communicate with each other in a water-tight manner, cooling water directed from the lower end of the water supply pipe 14 to the lower end of the water discharge pipe 15 is discharged to the outside through the water discharge pipe 15, the water discharge holes 21, the annular groove 31, the water discharge outer cylinder 13, the water discharge branch pipe 40 and the external cooling water discharge pipe (not shown). Thus, the sub-lance 3 is cooled by cooling water.

A probe for sampling and temperature-measuring of a molten metal is connected to the lowermost end of the air supply tube 16 (refer to FIGS. 2 and 3) as mentioned previously, and a swivel joint 32 for connecting an external gas supply pipe (not shown) rotatably engages with the upper end portion thereof. To prevent slag from coming into the probe when the probe passes through the slag layer covering the surface of the molten metal, pressurized gas such as air and nitrogen is blown into the probe from the gas supply pipe (not shown) through the swivel joint 32 and the air supply pipe 16. The swivel joint 32 is provided with a tapped hole 45 for taking out the lead wire of the probe, and the tapped hole 45 can be closed with a cap (not shown) when out of operation.

The air supply pipe 16 is fixed to the water discharge pipe 15 through a sealing mechanism 16a, and the water discharge pipe 15 is fixed to the water supply pipe 14 by a bolt 33. Since the air supply pipe 16, the water discharge pipe 15 and the water supply pipe 14 constituting the sub-lance 3 are thus fixed to each other, when rotating the sub-lance 3 around the axial line thereof in a manner as described later, the air supply pipe 16, the water discharge pipe 15 and the water supply pipe 14 rotate as an integral body. Further, since the water supply outer cylinder 12, the water discharge outer cylinder 13 and the swivel joint 32 rotatably engage respectively with the upper end portions of the water supply pipe 14, the water discharge pipe 15 and the air supply pipe 16, as mentioned previously, the water supply outer cylinder 12, the water discharge outer cylinder 13 and the swivel joint 32 never rotate together with the sub-lance 3.

Although the structure of the sub-lance 3 described in detail above, which is used in the present invention, is substantially the same as the structure of the sub-lance in said prior art, one of the features of the present invention lies in that the water supply branch pipe 39 of the water supply outer cylinder 12 and the water discharge branch pipe 40 of the water discharge outer cylinder 13 are integrally connected to each other by a fixing plate 41. An example in which the flange joint 25 of the water supply branch pipe 39 and the flange joint 30 of the water discharge branch pipe 40 are integrally connected by the fixing plate 41 are represented in FIG. 6 as a preferable embodiment. However, the present invention is not limited to this embodiment. The water supply branch pipe 39 and the water discharge branch pipe 40 may of course be integrally connected by the fixing plate 41 at a place near the water supply outer cylinder 12 and the water discharge outer cylinder 13.

Since, in the present invention, the water supply branch pipe 39 and the water discharge branch pipe 40 are integrally connected by the fixing plate 41 as mentioned above, the water supply outer cylinder 12 and the water discharge outer cylinder 13 are also integrally connected as a result. When, therefore, the sub-lance 3 is rotated in a manner as described later, the water supply outer cylinder 12 and the water discharge outer cylinder 13 do not rotate together with the sub-lance 3, but always remain stationary at a prescribed position. In this example, a pin 42 is welded to the lower surface of the water supply outer cylinder 12. When the sub-lance 3 is fitted to the sub-lance carriage 10, the pin 42 engages with a pin hole provided in a receiving stand 10a described later which is fixed to the sub-lance carriage 10, and thus more surely prevents the water supply outer cylinder 12 and the water discharge outer cylinder 13 from rotating together with the sub-lance 3. According to the present invention, therefore, it is possible to prevent strong non-uniform forces from acting on the respective sealing mechanisms between the water supply outer cylinder 12 and the water supply pipe 14, between the water discharge outer cylinder 13 and the water discharge pipe 15, and between the water supply pipe 14, the water discharge pipe 15 and the air supply 16, and from causing troubles in these sealing mechanisms, thus permitting sure prevention of cooling water leakage observed in said prior art.

In FIGS. 5 and 6, 17 is a drive mechanism including a reduction gear for rotating the sub-lance 3 around the axial line thereof. A chain 36 engages with a small sprocket 34 fitted to the axis of rotation of the drive mechanism 17 and with a large sprocket 35 fitted to the upper end portion of the water discharge pipe 15 so that the sub-lance 3 may be rotated by a desired angle around the axial line thereof by operating the drive mechanism 17. FIG. 6 illustrates a case where the drive mechanism 17 is fitted onto the outer surface of the water discharge outer cylinder 13 through a fitting rack 17a, whereas the sub-lance 3 may well be rotated by a mechanism similar to that mentioned above by fitting the drive mechanism 17 onto the outer surface of the water supply outer cylinder 12.

Although the aforementioned drive mechanism for the sub-lance 3, which is used in the present invention, is substantially the same as the drive mechanism for the sub-lance in said prior art, another feature of the present invention lies in that a sub-lance rotation angle detector is provided at the tip of the axis of rotation of the drive mechanism 17. More specifically, as shown in FIGS. 5 and 6, a sub-lance rotation angle detector 43 including a synchro device is provided at the tip of the axis of rotation of the drive mechanism 17 through a fitting rack 44. The indication of the sub-lance rotation angle detector 43 permits easy and accurate detection of an angle of rotation from the original position of the sub-lance 3 before rotation. Indication of the sub-lance rotation angle detector may well be based for example on a dial having a 360° calibration and a pointer, or on the recording on a chart paper. The actuation of the drive mechanism 17 can be automatically controlled by previously setting the sub-lance rotation angle detector 43 at a prescribed angle of rotation of the sub-lance 3, and when the sub-lance 3 rotates by the prescribed angle, feeding back a signal to the drive mechanism 17.

In the present invention, as mentioned above, the angle of rotation of the sub-lance 3 by the drive mechanism 17 can be easily and accurately detected. It is therefore possible to accurately rotate the sub-lance 3 by the most appropriate angle of rotation for correcting a deflection of the sub-lance 3 toward the main lance, which occurs during refining of molten metal in a converter.

In FIGS. 5 and 6, 37 is a suspension fitting fixed to the upper end portion of the water discharge outer cylinder 13. In the same manner as described as to said prior art, the sub-lance 3 is engaged with or disengaged from the sub-lance carriage 10 by hoisting up or down the suspension fitting 37 with the use of a crane (not shown). More specifically, the sub-lance 3 can be fitted to the sub-lance carriage 10 by inserting the sub-lance 3, by hoisting down with the use of the crane, into a hole or a notch in the receiving stand 10a fixed to the upper end portion of the sub-lance carriage 10 and into an opening in a supporting device 38 fixed to the lower end portion of the sub-lance carriage 10. The sub-lance 3 can be easily removed from the sub-lance carriage 10 by hoisting up the sub-lance 3 thus fitted to the sub-lance carriage 10 with the use of the crane. The present invention has a further feature in that the alignment for holding the sub-lance 3 accurately in the vertical position and the prevention of swinging of the sub-lance 3 are facilitated by the improvement of the above-mentioned supporting device 38.

Since the receiving stand 10a for supporting the sub-lance 3 fixed to the upper end portion of the sub-lance carriage 10 is substantially the same as that in the prior art, the description of the receiving stand 10a is omitted here. Only, the sub-lance supporting device 38 of the present invention fixed to the lower end portion of the sub-lance carriage 10 is described below.

Figure 7:
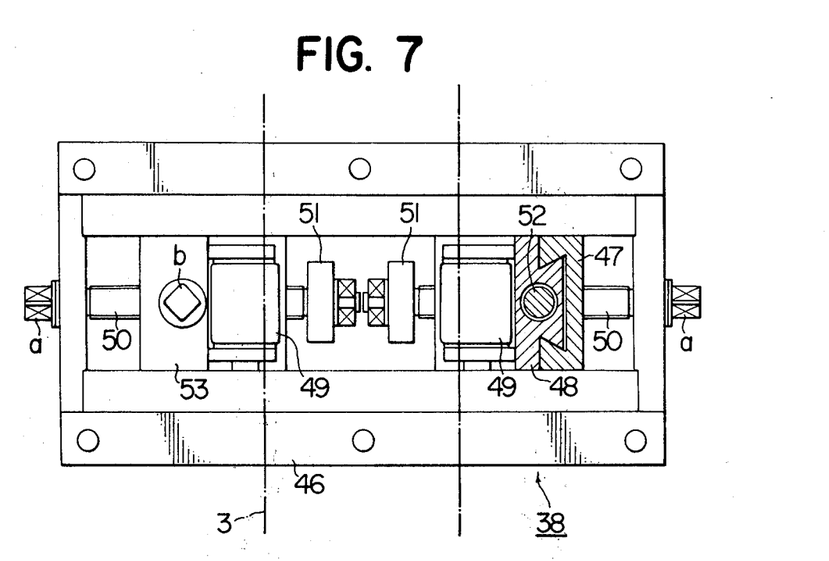
FIG. 7 is a partial cutaway front view illustrating an embodiment of the sub-lance supporting device in the sub-lance assembly of the present invention.
Figure 8:
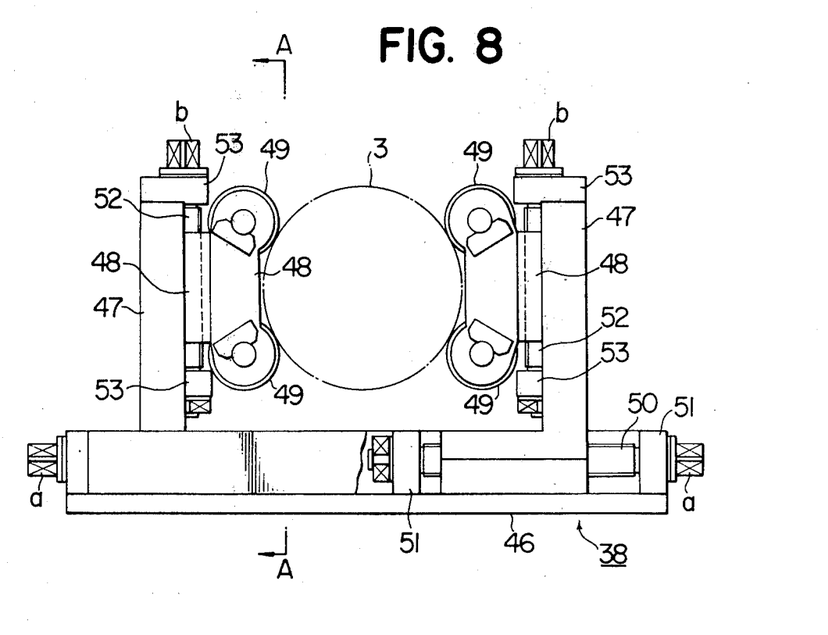
FIG. 8 is a partial cutaway plan view illustrating an embodiment of the sub-lance supporting device in the sub-lance assembly of the present invention; and, FIG. 9 is a sectional view of FIG. 8 as cut along line A—A.

FIG. 7 is a partial cutaway front view of an embodiment of the supporting device for the sub-lance of the present invention, FIG. 8, a partial cutaway plan view thereof, and FIG. 9, a sectional view of FIG. 8 as cut along line A—A.

In FIGS. 7 through 9, 46 is a rectangular base plate to be fixed to the sub-lance carriage 10. The base plate 46 is fixed, with its shorter sides in the vertical position, to the lower end portion of the sub-lance carriage 10. The base plate 46 is provided with a pair of sliding members 47 which are slidable in the longitudinal direction on the surface of the base plate 46, in parallel with the shorter sides of the base plate 46, so that the two sliding members 47 face straight each other. Each of the sliding members 47 engages with the space between the base plate 46 and a cover 54 fixed to the base plate 46. Each of the sliding members 47 is provided with a dovetail groove extending in the direction perpendicular to the surface of the base plate 46 on each surface facing the other, and a roller support 48 engages with said dovetail groove slidably along said dovetail groove. The respective roller supports 48, i.e., the two roller supports face straight each other. A pair of rotating rollers 49, each having an axis of rotation in parallel with the axial line of the sub-lance 3 to be inserted, is rotatably fitted to each of the roller supports 48. The respective pairs of rotating rollers 49, i.e., the two pairs of rotating rollers 49 also face straight each other. The two pairs of rotating rollers 49, i.e., the four rotating rollers 49 clamp the inserted sub-lance 3 in a manner as described later, and rotate in contact with the sub-lance 3 in response to the rotation of the sub-lance 3.

A screw shaft 50 having a center axis parallel to the longer sides of the base plate 46 is screw-connected to each of the sliding members 47. Both ends of the screw shaft 50 are rotatably supported by a pair of stoppers 51 fixed to the base plate 46. By turning a knob "a" at an end of the screw shaft 50, therefore, each of the sliding members 47 slides on the surface of the base plate 46 in the longitudinal direction of the base plate 46 in response to the amount of turning.

A screw shaft 52 having a center axis parallel to the perpendicular direction to the surface of the base plate 46 is screw-connected to each of the roller supports 48. The both ends of the screw shaft 52 are rotatably supported by a pair of stoppers 53 fixed to the sliding members 47. By turning a knob "b" at an end of the screw shaft 52, therefore, each of the roller supports 48 slides in the direction perpendicular to the surface of the base plate 46 in response to the amount of turning.

The sub-lance 3 is supported and aligned by operating in the following manner the supporting device 38 constructed as mentioned above:

(1) first, as mentioned previously with reference to FIGS. 5 and 6, inserting the sub-lance 3 into the hole or the notch in the receiving stand 10a fixed to the upper end portion of the sub-lance carriage 10, by operating the crane (not shown);

(2) then, inserting the sub-lance 3 into the space between the pair of sliding members 47 previously spaced apart by turning the pair of screw shafts 50, hence between the four rotating rollers 49, and thus fitting the sub-lance 3 to the sub-lance carriage 10;

(3) then, causing the pair of sliding members 47 to slide to approach to each other by turning the pair of screw shafts 50, and in the mean time, bringing the two pairs of rotating rollers 49 into contact with the sub-lance 3 through sliding of the pair of roller supports 48 by turning the pair of screw shafts 52, and thus, clamping the sub-lance 3 with four rotating rollers 49;

(4) subsequently, with a view to holding the sub-lance 3 accurately in the vertical position, adjusting the position of the pair of sliding members 47 and the pair of roller supports 48, hence of the two pairs of rotating rollers 49 by turning the pair of screw shafts 50 and the pair of screw shafts 52.

In this manner, the sub-lance 3 is aligned by the supporting device 38 so that the sub-lance 3 accurately keeps its vertical position, with the receiving stand 10a at the upper end portion of the sub-lance carriage 10 as the fulcrum.

As is clear from the above description, the sliding directions of the sliding members 47 and the roller supports 48 of the supporting device 38 of the present invention intersect at right angles on a horizontal plane. This permits complete alignment for holding the sub-lance 3 accurately in the vertical position. Operation of the screw shafts 50 and 52 may be either manual or by a remote operation by providing a drive mechanism for this purpose.

The sub-lance 3 is considerably long as mentioned previously. Therefore, with a view to preventing swinging of the sub-lance 3 and improving the accuracy of aligning adjustment of the sub-lance 3, it is desirable to fix the receiving stand 10a as close as possible to the upper end of the sub-lance carriage 10, and the supporting device 38 as close as possible to the lower end of the sub-lance carriage 10.

According to the sub-lance assembly of the present invention described in detail above, it is possible:

(a) to easily and accurately detect the angle of rotation of the sub-lance, and hence to ensure correction of the deflection of the sub-lance;

(b) to ensure prevention of leakage of cooling water for cooling the sub-lance; and (c) to ensure easy aligning adjustment for holding the sub-lance accurately in the vertical position, as well as to prevent swinging of the sub-lance; thus providing industrially useful effects.

What is claimed is:

1. In a sub-lance assembly for sampling and temperature-measuring of molten metal during refining, which comprises:
    a sub-lance having a concentric three-pipe structure comprising from inside to outside an air supply pipe, a water discharge pipe and a water supply pipe, said sub-lance being releasably fitted to a sub-lance carriage in the substantially vertical position by a receiving stand fixed to the upper end portion of said sub-lance carriage and a supporting device fixed to the lower end portion of said sub-lance carriage;
    a water supply outer cylinder having a water supply branch pipe, rotatably engaging with the upper end portion of said water supply pipe through a bearing mechanism and a sealing mechanism, said water supply pipe, said water supply outer cylinder and said water supply branch pipe communicating with each other in a water-tight manner;
    a water discharge outer cylinder having a water discharge branch pipe, rotatably engaging with the upper end portion of said water discharge pipe through a bearing mechanism and a sealing mechanism, said water discharge pipe, said water discharge outer cylinder and said water discharge branch pipe communicating with each other in a water-tight manner, said water discharge outer cylinder being located above said water supply outer cylinder; and
    a drive mechanism for rotating said sub-lance around the axial line thereof, said drive mechanism being fitted onto one of the outer surfaces of said water supply outer cylinder and said water discharge outer cylinder;

the improvement comprising:
    a sub-lance rotation angle detector provided at the tip of the axis of rotation of said drive mechanism, said rotation angle detector being adapted to detect the angle of rotation of said sub-lance, and
    a fixing plate integrally connecting said water supply branch pipe and said water discharge branch pipe, said fixing plate being located at a place near said water supply outer cylinder and said water discharge outer cylinder, said fixing plate being adapted, when rotating said sub-lance by said drive mechanism, to prevent said water supply outer cylinder and said water discharge outer cylinder from rotating together with said sub-lance.

2. The sub-lance assembly as claimed in claim 1, wherein said supporting device comprises:
    a rectangular base plate, said base plate being fixed, with its shorter sides in the vertical position, to the lower end portion of said sub-lance carriage;
    a cover fixed to said base plate with a space between said base plate and at least a portion of said cover;
    a pair of sliding members, said pair of sliding members being slidably provided on the surface of said base plate in parallel with the shorter sides of said base plate, so that said pair of sliding members face each other, each of said pair of sliding members engaging with the space between said base plate and said cover fixed to said base plate, each of said pair of sliding members being adapted to slide on the surface of said base plate in the longitudinal direction thereof, each of said pair of sliding members having a dovetail groove extending in the direction perpendicular to the surface of said base plate on each surface facing the other;
    a pair of screw shafts for the sliding members, each of said pair of screw shafts being screw-connected to each of said pair of sliding members in parallel with the longitudinal direction of said base plate, each of said pair of screw shafts being adapted to cause each of said pair of sliding members to so slide in response to turning thereof;
    a pair of roller supports, each of said pair of roller supports engaging with said dovetail groove of each of said pair of sliding members, said pair of roller supports facing each other, each of said pair of roller supports being adapted to slide along said dovetail groove in the direction perpendicular to said base plate;
    a second pair of screw shafts for the roller support, each of said second pair of screw shafts being screw-connected to each of said pair of roller supports in the direction perpendicular to said base plate, each of said second pair of screw shafts being adapted to cause each of said pair of roller supports to so slide in response to turning thereof;
    two pairs of rotating rollers, each pair of said two pairs of rotating rollers being fitted to each of said pair of roller supports, said two pairs of rotating rollers facing each other, the axis of rotation of each of said two pairs of rotating rollers being parallel to the axial line of said sub-lance inserted, said two pairs of rotating rollers being rotatable and being adapted to come in contact with said sub-lance and clamp same by turning said pair of screw shafts for the sliding member and said second pair of screw shafts for the roller support;

thereby said supporting device being adapted to permit aligning adjustment for holding said sub-lance substantially in the vertical position and to prevent swinging of said sub-lance, in cooperation with said receiving stand fixed to the upper end portion of said sub-lance carriage.

3. The sub-lance assembly as claimed in claim 1, wherein:

a pin is fixed to the lower surface of said water supply outer cylinder, and when said sub-lance is fitted to said sub-lance carriage, said pin is inserted into a pin hole provided in said receiving stand fixed to the upper end portion of said sub-lance carriage, thereby more surely preventing said water supply outer cylinder and said water discharge outer cylinder from rotating together with said sub-lance.

4. The sub-lance assembly as claimed in claim 2, wherein:

a pin is fixed to the lower surface of said water supply outer cylinder, and when said sub-lance is fitted to said sub-lance carriage, said pin is inserted into a pin hole provided in said receiving stand fixed to the upper end portion of said sub-lance carriage, thereby more surely preventing said water supply outer cylinder and said water discharge outer cylinder from rotating together with said sub-lance.

* * * * *